(12) United States Patent
Lanier et al.

(10) Patent No.: US 8,900,198 B2
(45) Date of Patent: Dec. 2, 2014

(54) DEVICE FOR PROTECTING AN INJECTION APPARATUS, IN PARTICULAR AN INJECTION APPARATUS FOR MEDICAL USE, SUCH AS A SYRINGE

(75) Inventors: Romain Lanier, Grenoble (FR); Gregory Peruzzo, Prunieres (FR)

(73) Assignee: Becton Dickinson France, Le Pont de Claix (FR)

( * ) Notice: Subject to any disclaimer, the term of this patent is extended or adjusted under 35 U.S.C. 154(b) by 673 days.

(21) Appl. No.: 12/864,974

(22) PCT Filed: Jan. 14, 2009

(86) PCT No.: PCT/IB2009/050134
§ 371 (c)(1),
(2), (4) Date: Oct. 25, 2010

(87) PCT Pub. No.: WO2009/095805
PCT Pub. Date: Aug. 6, 2009

(65) Prior Publication Data
US 2011/0034880 A1 Feb. 10, 2011

(30) Foreign Application Priority Data
Jan. 28, 2008 (FR) ..................................... 08 00430

(51) Int. Cl.
*A61M 5/32* (2006.01)
*A61M 5/00* (2006.01)

(52) U.S. Cl.
CPC ............. *A61M 5/326* (2013.01); *A61M 5/3271* (2013.01); *A61M 2005/3247* (2013.01); *A61M 2005/3261* (2013.01)

USPC ............................ 604/198; 604/110; 604/192

(58) Field of Classification Search
USPC .................................. 604/110, 192, 198, 263
See application file for complete search history.

(56) References Cited

U.S. PATENT DOCUMENTS 7,682,344 B2    3/2010  Barrelle
2005/0033230 A1* 2/2005  Alchas et al. ................. 604/117

FOREIGN PATENT DOCUMENTS

| WO | 99/17823  | A1 | 4/1999  |
|----|-----------|----|---------|
| WO | 01/85239  | A2 | 11/2001 |
| WO | 02/083205 | A1 | 10/2002 |
| WO | 02/098494 | A2 | 12/2002 |
| WO | 03/013632 | A2 | 2/2003  |

* cited by examiner

Primary Examiner — Kevin C Sirmons
Assistant Examiner — Shefali Patel
(74) Attorney, Agent, or Firm — Hoffmann & Baron, LLP

(57) ABSTRACT

A device comprising a body, a sleeve mobile in relation to the body, and a lock enabling locking of the sleeve in a protective position; the sleeve can be moved between a non-protective position, in which an injection member is exposed, and the protective position; the lock comprising at least one flexible proximal leg. According to the invention, the at least one leg comprises at least one bearing surface and the device comprises at least one corresponding bearing surface, these respective bearing surfaces being able to bear against each other when a stress is exerted on the sleeve in a direction tending to return the sleeve toward the non-protective position.

7 Claims, 3 Drawing Sheets

DEVICE FOR PROTECTING AN INJECTION APPARATUS, IN PARTICULAR AN INJECTION APPARATUS FOR MEDICAL USE, SUCH AS A SYRINGE

CROSS-REFERENCES TO RELATED APPLICATIONS

This application is a national stage entry of PCT/IB09/50134, filed on Jan. 14,2009, which claims priority to application 0800430, filed in France, on Jan. 28, 2008.

BACKGROUND OF THE INVENTION

1. Field of the Invention

The present invention concerns a device for protecting an injection device, in particular an injection device for medical use such as a syringe.

2. Description of Related Art

In this application, the distal end of a part or of the device is considered to be the end farthest away from the injection site. Likewise, in this application, the term "distal direction" refers to the direction of injection, and "proximal direction" designates the direction opposite the direction of injection.

It is known to provide a device for protecting an injection device comprising a body in which the injection device is placed, a sleeve mobile in relation to this body, means enabling the mobility of this sleeve and means enabling the sleeve to be locked in the protective position. The sleeve can be moved between a non-protective position, in which an injection member comprised by the injection device is exposed so as to allow injection, and a protective position, in which the sleeve completely covers the injection member so as to eliminate the risk of contamination of the user by this injection member and to prevent reuse of the injection device. Said injection member is the needle of this syringe when the injection device is a syringe.

Document WO 2005/030301, in the applicant's name, illustrates one such protection device. In this known device, as illustrated by the appended FIG. 1, the means allowing locking of the sleeve 3A in the protective position comprise at least one flexible proximal leg 7A integral with the sleeve 3A, being engaged, in the protective position, behind a corresponding distal edge 51A arranged at the end of a rib 5A integral with said body. The sleeve 3A also comprises, at its proximal part, at least one wall 10A adjacent to the leg 7A, which protrudes in the proximal direction.

The flexible leg 7A has a relatively significant length (it is also part of the means allowing the mobility of the sleeve 3A, being, in the non-protective position, hooked on a proximal rim formed by the rib 5A and, at the end of injection, being bent by a cam surface actuated by the piston rod so as to be freed from this rim). It also has a relatively reduced thickness, such that it can assume a position between the body of the syringe and the body of the device, and is in a material having a degree of elastic flexibility, so that it can be deformed between its hooked position making it possible to maintain the sleeve 3A in the non-protective position and its unhooked position allowing movement of this sleeve 3A toward the protective position.

This flexible leg 7A has the drawback of presenting limited resistance to a force exerted on it longitudinally, having been evaluated at 60 N. This limited resistance does not exclude the possibility of forcing the sleeve 3A toward said non-protective position, the leg 7A then being subject to buckling, i.e. the phenomenon defined by a breaking or bending of the leg subjected to compressive efforts in the direction of its length. This buckling generally leads to irreversible damage to the leg 7A, such that said leg, after a first forcing, no longer adequately maintains the sleeve 3A in the protective position.

Moreover, it has been noted that the resistance value of this leg 7A varies substantially within a same sample of a plurality of devices as the buckling phenomenon is not very repeatable and is poorly controlled. The result is that certain devices from this sample have too limited a resistance to said forcing to effectively provide the desired protection.

The present invention aims to resolve these essential drawbacks, without, however, calling into question the use of the structure of the protection device as previously stated, known by the earlier document mentioned above.

BRIEF SUMMARY OF THE INVENTION

The concerned device comprises, in a known manner, a body in which the injection device is placed, a sleeve mobile in relation to said body, means for moving said sleeve in relation to the body, and locking means allowing locking of the sleeve in a protective position; the sleeve can be moved between a non-protective position, in which an injection member comprised by the injection device is exposed so as to allow injection, and said protective position, in which the sleeve completely covers the injection member; said locking means comprise at least one flexible proximal leg integral with the sleeve, forming a first bearing surface by which this leg engages, in said protective position, behind at least a first corresponding distal bearing surface of said body.

According to the invention, the leg comprises at least one additional bearing surface, and the device comprises at least one corresponding additional bearing surface, these respective additional bearing surfaces being able to bear against each other when a force is exerted on the sleeve in the direction tending to return this sleeve toward said non-protective position.

The additional bearing surfaces thus arranged make it possible to increase the bearing surface of the leg with the rest of the device and therefore to better distribute the surface on which the force undergone by the leg is exerted during an action tending to return the sleeve to the non-protective position. The result is that the leg according to the invention has greatly increased resistance relative to that of the device according to the prior art, which makes it possible to effectively prevent all attempts to force the sleeve toward its non-protective position. Moreover, within a same sample of a plurality of devices, the resistance measured to such a forcing has shown itself to be greatly sufficient to obtain the desired protection in all cases.

The leg and the device may each comprise an additional bearing surface arranged substantially transversely relative to the axis of the sleeve, the two bearing surfaces constraining the leg along the longitudinal direction of said leg when they bear against each other.

The leg and the device may also each comprise an additional bearing surface arranged substantially longitudinally relative to the axis of the sleeve, these two additional bearing surfaces constraining the leg along the circumferential direction of said leg when they bear against each other.

Preferably, the leg comprises two additional bearing surfaces, a first of which is arranged so as to constrain the leg along the longitudinal direction of said leg and the second of which is arranged so as to constrain the leg in the circumferential direction, the device comprising two corresponding additional bearing surfaces.

The leg and the device thus form double additional bearing surfaces, namely one bearing taking place in the longitudinal direction of the leg and the other bearing taking place in the circumferential direction. The leg is thus simultaneously supported by these two bearings, which further increases its resistance to buckling.

Preferably, said additional bearing surfaces of the leg and the device are arranged in a location located substantially between one-third and two-thirds of the length of the leg (i.e. the dimension of the latter extending along the axis of sliding of the sleeve).

The arrangement of these additional bearing surfaces in this location makes it possible to effectively oppose the risk of buckling of the leg, said leg being supported by these bearing surfaces located substantially at the level of its median area, i.e. at its area the most in a position to be subject to buckling.

According to one preferred embodiment of the invention, the leg has an enlarged upper portion, forming an extension in the circumferential direction, this extension having a lower edge which forms said first additional bearing surface and an end edge in the circumferential direction, which forms said second additional bearing surface, and the sleeve comprises at least one proximal wall located in the vicinity of the leg, having a notch forming a first rim, which extends substantially in the transverse direction relative to the axis of sliding of the sleeve and which is able to cooperate with said first additional bearing surface of the leg, and a second rim, which extends substantially in the longitudinal direction relative to the axis of sliding of the sleeve and which is able to cooperate with said second additional bearing surface of the leg.

According to another embodiment of the device:

the leg comprises a tilted edge extending over the entirety of its length, forming one said additional bearing surface comprised by this leg, and the device comprises at least one wall having a tilted edge extending over the entire length of this wall, forming one said additional bearing surface comprised by this device.

According to one possibility, the leg, when it is intended to be elastically deformed to engage behind said first distal bearing surface, comprises an area having a reduced cross-section, located away from said additional bearing surfaces.

This area having a reduced cross-section makes it possible to increase the flexibility of the leg so as to promote its engagement behind said first distal bearing surface; this flexibility also makes it possible to promote the coming of said additional bearing surface(s) into mutual cooperation when the leg is subject to the force generated by the action returning the sleeve to the non-protective position. In particular, when it is necessary to provide for clearances between said additional bearing surfaces to enable engagement of the leg behind said first distal bearing surface, said area having a reduced cross-section may be subject to compression in the longitudinal direction of the leg ensuring elimination of these clearances and therefore the perfect coming into mutual contact of the additional bearing surfaces.

BRIEF DESCRIPTION OF THE DRAWINGS

The invention will be well understood, and other characteristics and advantages thereof will appear, in reference to the appended diagrammatic drawing, illustrating, as a non-limiting example, one preferred embodiment of the device it concerns.

DETAILED DESCRIPTION OF THE INVENTION

For simplification, the parts or elements of one embodiment which are found identically or similarly in another embodiment will be identified using the same numerical references and will not be described again.

Figure 2:
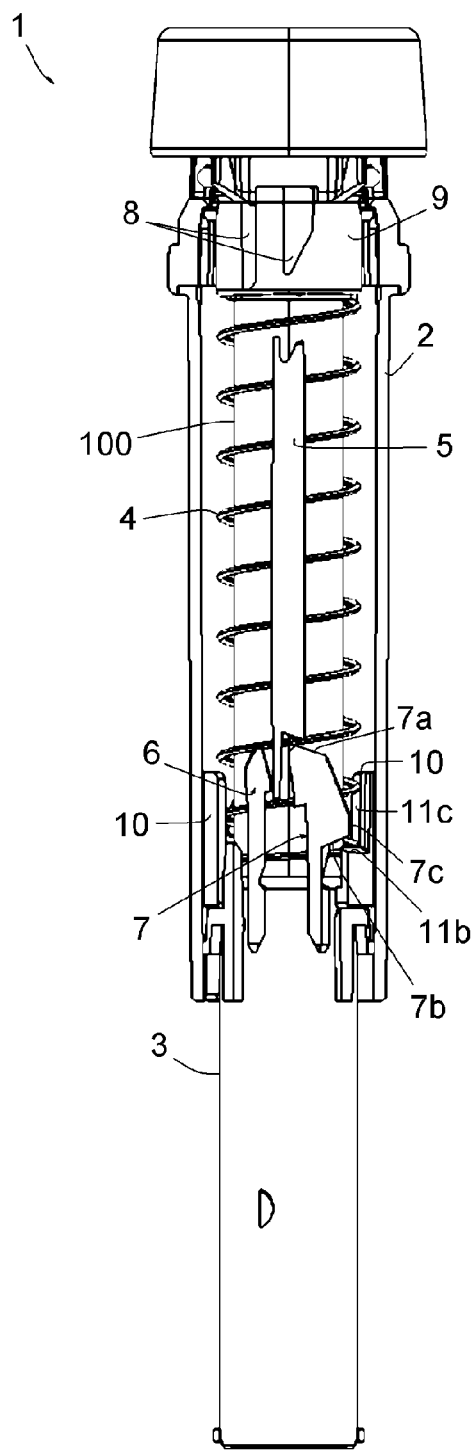
FIG. 2 is a side view, in longitudinal cross-section going through its axis, according to a first embodiment.
Figure 3:
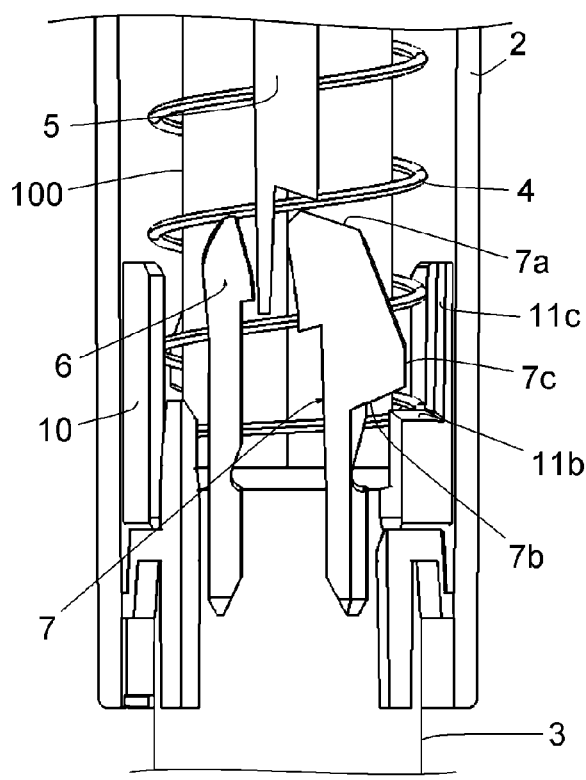
FIG. 3 is a partial view, similar to FIG. 2, at a larger scale, showing the distal part of the body it comprises and the proximal part of a sleeve which it also comprises.

FIGS. 2 and 3 illustrate a device 1 for protecting an injection device, in particular an injection device for medical use, which, in the illustrated example, is a syringe.

The device 1 comprises a body 2 in which are placed the syringe body 100, a sleeve 3 mobile in relation to this body 2, a spring 4 for moving this sleeve 3 in relation to the body 2, and a locking assembly 5, 6, 7 enabling locking of the sleeve 3 in the illustrated position, called the "protective position".

In general, the device is very similar to that described in document WO 2005/030301, in the applicant's name, to which one may refer for more detailed explanations.

The body 2 is tubular and has a length such that it can house the syringe body 100, but that the needle of this syringe protrudes beyond the distal end of said body 2 when the sleeve 3 is in a "non-protective" position. In this position, the sleeve 3 is completely drawn into the body 2, assuming a position between the wall of the latter and the syringe body 100, and the spring 4, inserted between the sleeve 3 and a proximal ring which receives the body 2, is stressed.

The body 2 comprises two diametrically opposed ribs 5, integral with said body and protruding inwardly, one of which is illustrated in FIGS. 2 and 3 notwithstanding the longitudinal cross-section of the body 2. Each rib 5 comprises notched ends designed to cooperate with a pair of proximal legs 6, 7 comprised by the sleeve 3, in the same way as described in the aforementioned document WO 2005/030301. In summary, in said non-protective position, these proximal legs 6 and 7 hook on the proximal end of the rib 5, and thereby ensure maintenance of the sleeve 3 in this position notwithstanding the elastic return force of the spring 4; at the end of injection, these legs 6, 7 are elastically deformed by cam-shaped projections 8 arranged on a proximal ring 9, itself moved by the piston rod of the syringe, such that they are unhooked from the rib 5; the sleeve 3 thus being freed, the spring 4 relaxes and brings this sleeve 3 into the illustrated protective position, in which the sleeve 3 completely covers the needle of the syringe; among the two legs 6, 7, the leg 7 illustrated on the right in FIGS. 2 and 3 slides along the rib 5 and, when the sleeve 3 reaches said protective position, engages through elastic return in the distal notch formed by the rib 5. A first bearing surface 7a comprised by this leg 7 at its proximal end then comes into the vicinity of a rim of the rib 5 defining said distal notch, thereby locking the sleeve 3 in the protective position.

Figure 4:
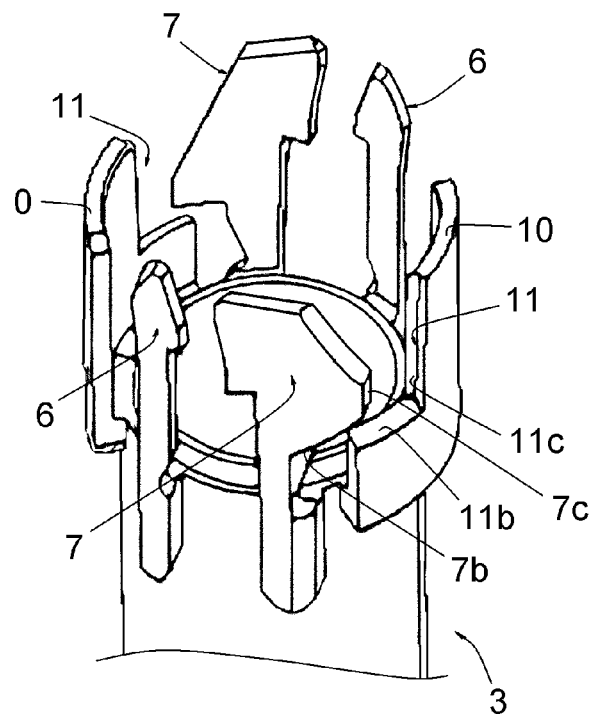
FIG. 4 is a perspective view of the proximal portion of the sleeve.
Figure 5:
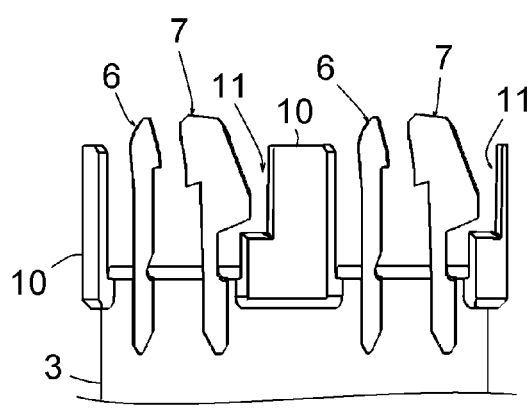
FIG. 5 is a side view of this proximal portion.

Besides the legs 6 and 7, the sleeve 3 comprises, at its proximal part, as shown more particularly by FIGS. 3 to 5, fixed walls 10 adjacent to the legs 7, which project in the proximal direction.

Figure 1:
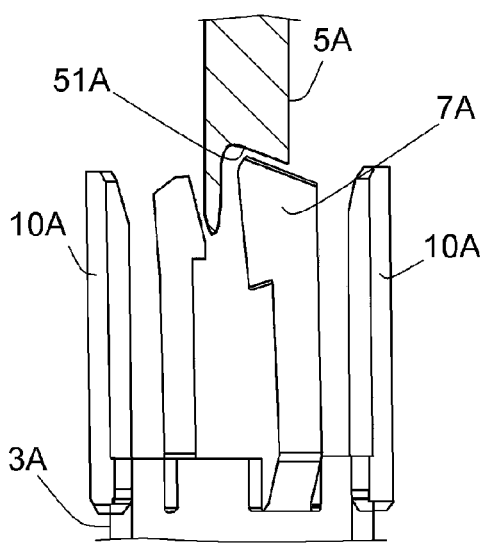
FIG. 1 is a side view of a prior art arrangement.

As appears by comparing FIG. 1 on one hand and 2 to 5 on the other, it appears that each leg 7 and adjacent wall 10 shown in FIGS. 2 to 5 has a shape which differs from those of the corresponding leg 7A and the protruding wall 10A of the device according to the prior art illustrated in FIG. 1.

Indeed, the leg 7 illustrated in FIGS. 2 to 5 has an enlarged upper portion, forming an extension in the circumferential direction, this extension having a lower edge 7b which forms a first additional bearing surface and an end edge in the circumferential direction 7c, which forms a second additional bearing surface. The bearing surface formed by the edge 7b is arranged substantially transversely in relation to the axis of the sleeve 3 and the bearing surface formed by the edge 7c is arranged substantially longitudinally in relation to the axis of the sleeve 3. These bearing surfaces are arranged substantially halfway up the leg 7.

The adjacent wall 10 has, on its side adjacent to the leg 7, a rectangular notch 11 forming a rim 11b which extends substantially in the transverse direction relative to the axis of sliding of the sleeve 3 and a rim 11c which extends substantially in the longitudinal direction relative to the axis of sliding of the sleeve 3.

Figure 6:
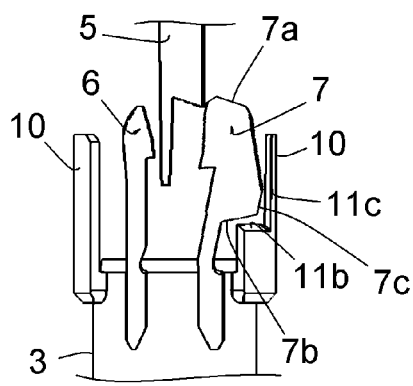
FIGS. 6 to 8 are views of this proximal portion and a rib comprised by said body for locking the sleeve in three positions relative to said body.
Figure 7:
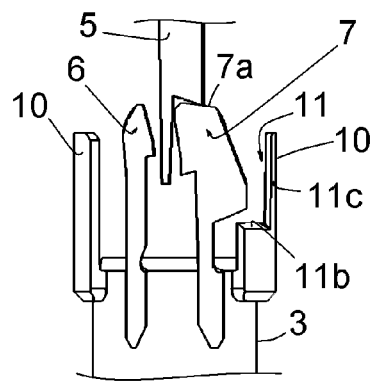
Figure 8:
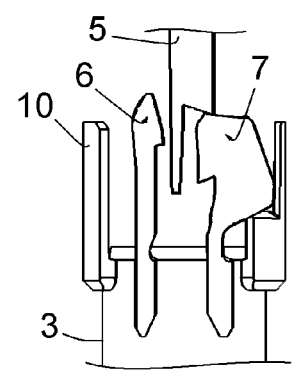

As appears in reference to FIGS. 6 to 8, the notch 11 enables engagement of the leg 7 in the distal notch of the rib 5 notwithstanding the increased width of the proximal portion of this leg 7 (cf. FIGS. 6 and 7).

When stress is exerted on the sleeve 3 in the direction bringing this sleeve 3 back toward said non-protective position, the leg 7 tends to compress longitudinally. The respective additional bearing surfaces 7b, 7c and 11b, 11c then bear against each other (cf. FIG. 8), the surfaces 7b, 11b constraining the leg 7 according to the longitudinal direction of this leg and the surfaces 7c, 11c constraining the leg 7 according to the circumferential direction of the sleeve 3. These surfaces 7b, 7c and 11b, 11c thus make it possible to increase the bearing surface of the leg 7 with the rest of the device 1 and therefore to better distribute the surface on which the stress undergone by the leg 7 is exerted during an attempt to force the sleeve 3 toward the non-protective position; moreover, the constraints of the leg 7 produced by these bearing surfaces take place at the median area of the leg 7, i.e. at the area of said leg most likely to undergo buckling.

As a result of the arrangement of these additional bearing surfaces, the leg 7 has, relative to that of the device according to the prior art, greatly increased resistance, which makes it possible to effectively oppose forcing of the sleeve 3 toward the non-protective position. Moreover, within a same sample of a plurality of devices 1, the measured resistance to such forcing showed itself to be largely sufficient to obtain the desired protection in all cases.

Figure 9:
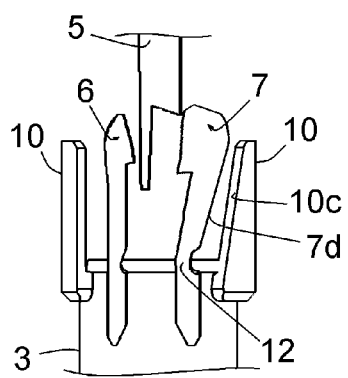
FIGS. 9 to 11 are views similar to FIGS. 6 to 8, respectively, of said proximal portion and said locking rib, according to a second embodiment of a locking leg comprised by this proximal portion.
Figure 10:
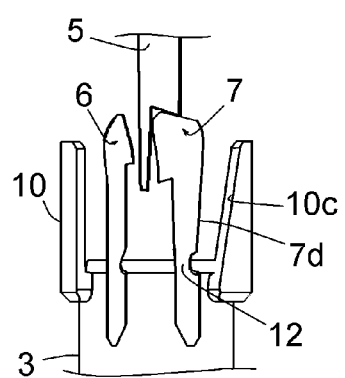
Figure 11:
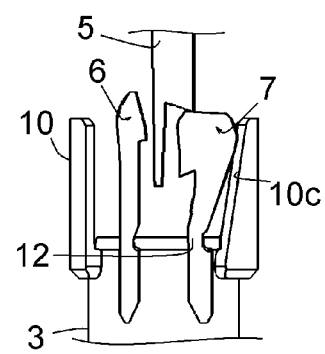

FIGS. 9 to 11 illustrate another embodiment of the device 1, in which the leg 7 has, from the side of the wall 10, a rectilinear tilted edge 7d extending over its entire length, while the wall 10 has, instead and in place of the notch 11, a tilted rectilinear edge 10c also extending over its entire length.

As shown in FIG. 11, upon an attempt to force the sleeve 3 toward the non-protective position, the tilted edge 7d realizes extended bearing against the edge 10c of the wall 10. The surface of this bearing increases as the intensity of the forcing increases.

In this other embodiment, the leg 7 comprises an area 12 having a reduced cross-section, located at its base, i.e. away from the additional bearing surfaces formed by the edges 7d and 10c.

This area 12 makes it possible to increase the flexibility of the leg 7 in order to promote its engagement in the distal notch of the rib 5; this flexibility also makes it possible to promote the mutual cooperation of said additional bearing surfaces 7d, 10c when the leg 7 undergoes the stress generated by the action tending to return the sleeve 3 to the non-protective position. In particular, when it is necessary to provide for clearances between said additional bearing surfaces 7d, 10c to enable engagement of the leg 7 in the distal notch of the rib 5, the area 12 may undergo compression in the longitudinal direction of the leg 7 ensuring the elimination of these clearances and therefore perfect mutual contact of the bearing surfaces 7d, 10c.

It appears from the preceding that the invention provides a device for protecting an injection device, in particular an injection device for medical use such as a syringe which, relative to the similar devices of the prior art, has determining advantages, described above.

The invention has been described in reference to embodiments provided purely as examples. It goes without saying that it is not limited to these embodiments, but that it extends to all embodiments covered by the appended claims.

The invention claimed is:

1. A device for protecting an injection device, the device comprising a body in which the injection device is placed, a sleeve mobile in relation to said body, means for moving the sleeve in relation to the body, and locking means making it possible to lock the sleeve in a protective position; the sleeve movable between a non-protective position, in which an injection member mounted on the injection device is exposed so as to allow injection, and said protective position, in which the sleeve completely covers the injection member; said locking means comprise at least one flexible proximal leg integral with, and compressible longitudinally relative to, the sleeve, forming a first bearing surface through which said at least one leg engages, in said protective position, behind at least a first corresponding distal bearing surface arranged of said body so as to constrain movement of the sleeve toward said non-protective position;

characterized in that the at least one leg comprises at least one additional bearing surface arranged thereon, and in that the device comprises at least one corresponding additional bearing surface circumferentially spaced out of longitudinal alignment with said first corresponding distal bearing surface, said respective additional bearing surfaces being able to bear against each other when a force is exerted on the sleeve in a direction tending to return the sleeve toward said non-protective position so as to constrain at least movement of said at least one leg in a circumferential direction.

2. The device according to claim 1, characterized in that said respective additional bearing surfaces are arranged substantially transversely relative to an axis of the sleeve so as to constrain along a longitudinal direction of said at least one leg when they bear against each other.

3. The device according to claim 1, characterized in that the at least one leg comprises two of the at least one additional bearing surface, a first of which is arranged so as to constrain the at least one leg along a longitudinal direction of said at least one leg and the second of which is arranged so as to constrain the at least one leg in the circumferential direction, the device comprising two of the at least one corresponding additional bearing surface.

4. The device according to claim 3, characterized in that:
the at least one leg has an enlarged upper portion, forming an extension in the circumferential direction, the extension having a lower edge which forms said first additional bearing surface and an end edge in the circumferential direction, which forms said second additional bearing surface, and
the sleeve comprises at least one proximal wall located in a vicinity of the at least one leg, presenting a notch forming a first rim, extending substantially in a transverse direction relative to an axis of sliding of the sleeve, able to cooperate with said first additional bearing surface of the at least one leg, and a second rim, extending substantially in the longitudinal direction relative to the axis of sliding of the sleeve, able to cooperate with said second additional bearing surface of the at least one leg.

5. The device according to claim 1, characterized in that said respective additional bearing surfaces of the at least one leg and the device are arranged in a location located substantially between one-third and two-thirds of a length of the at least one leg.

6. The device according to claim 1, characterized in that:
the at least one leg comprises a tilted edge extending over its entire length, forming one said at least one additional bearing surface comprised by said at least one leg, and
the device comprises at least one wall having a tilted rectilinear edge also extending over an entire length of the at least one wall, forming one said at least one corresponding additional bearing surface of the device.

7. The device according to claim 1, characterized in that the at least one leg comprises an area having a reduced cross-section, located away from said at least one additional bearing surface.

* * * * *